(12) United States Patent
Millan et al.

(10) Patent No.: US 7,723,304 B2
(45) Date of Patent: May 25, 2010

(54) SYSTEMS FOR DELIVERY AND RELEASE OF ANGIOTENSIN-(1-7)

(75) Inventors: Rubén D. S. Millan, Belo Horizonte (BR); Robson A. S. Dos Santos, Belo Horizonte (BR); Fréderic J. G. Frezad, Belo Horizonte (BR); Ana P. Nadu, Belo Horizonte (BR)

(73) Assignee: Universidade Federal De Minas Gerais—UFMG, Belo Horizonte (BR)

( * ) Notice: Subject to any disclaimer, the term of this patent is extended or adjusted under 35 U.S.C. 154(b) by 436 days.

(21) Appl. No.: 10/494,758

(22) PCT Filed: Nov. 5, 2002

(86) PCT No.: PCT/BR02/00156

§ 371 (c)(1),
(2), (4) Date: Nov. 30, 2004

(87) PCT Pub. No.: WO03/039434

PCT Pub. Date: May 15, 2003

(65) Prior Publication Data

US 2005/0069533 A1     Mar. 31, 2005

(30) Foreign Application Priority Data

Nov. 5, 2001    (BR) ................... 0105509

(51) Int. Cl.
*A61K 38/08* (2006.01)
(52) U.S. Cl. ...................................... 514/16
(58) Field of Classification Search ............... None
See application file for complete search history.

(56) References Cited

U.S. PATENT DOCUMENTS

| | | | |
|---|---|---|---|
| 4,054,736 A * | 10/1977 | Hayashi et al. | 536/103 |
| 4,078,052 A | 3/1978 | Papahadjopoulos | |
| 4,204,991 A | 5/1980 | Hallinan | |
| 4,224,179 A | 9/1980 | Schneider | |
| 4,235,871 A | 11/1980 | Papahadjopoulos | |
| 4,308,166 A | 12/1981 | Marchetti | |
| 4,310,506 A | 1/1982 | Baldeschweiler | |
| 4,394,372 A | 7/1983 | Tailor | |
| 4,485,054 A | 11/1984 | Mezei | |
| 4,508,703 A | 4/1985 | Redziniak | |
| 4,552,803 A | 11/1985 | Pearson | |
| 4,588,578 A | 5/1986 | Fountain | |
| 4,975,282 A | 12/1990 | Cullis | |
| 5,008,050 A | 4/1991 | Cullis | |
| 5,030,453 A | 7/1991 | Lenk | |
| 5,059,421 A | 10/1991 | Loughrey | |
| 5,126,333 A * | 6/1992 | Martini et al. | 514/58 |
| 5,169,637 A | 12/1992 | Lenk | |
| 5,236,944 A * | 8/1993 | Distelmans et al. | 514/397 |
| 2004/0171584 A1 | 9/2004 | Millan et al. | |
| 2005/0069533 A1 | 3/2005 | Millan et al. | |
| 2008/0108575 A1 | 5/2008 | Millan et al. | |

FOREIGN PATENT DOCUMENTS

| | | |
|---|---|---|
| DE | 2846200 | 4/1979 |
| GB | 2008122 | 5/1979 |
| GB | WO 03/039434 | 5/2003 |
| WO | WO 99/65465 | 12/1999 |
| WO | WO 01/44270 A2 * | 6/2001 |
| WO | WO 01/55176 | 8/2001 |

OTHER PUBLICATIONS

Al-Maghrebi et al., "Endogenous angiotensin -(1-7) reduces cardiac ischemia-induced dysfunction in diabetic hypertensive rats", Pharmacological Research, Dec. 22, 2008, pp. 263-268.

Grobe et al., "Prevention of angiotensin II-induced cardiac remodeling by angiotensin-(1-7)", the American Physiological Society, Nov. 6, 2006, pp. 2-8.

Langeveld et al., "Rescue of arterial function by angiotensin-(1-7): towards improvement of endothelial function by drug-eluting stents", Netherlands Heart Journal, Sep. 2008, pp. 1-6, vol. 16, No. 9.

Mercure et al., "Angiotensin(1-7) Blunts Hypertensive Cardiac Remodeling by a Direct Effect on the Heart", Circulation Research, Oct. 1, 2008, pp. 1319-1326, Dallas, Texas, US.

Uekama et al., "Cyclodextrin Drug Carrier Systems", American Chemical Society, 1998, pp. 2045-2076, Japan.

* cited by examiner

*Primary Examiner*—Andrew D Kosar
(74) *Attorney, Agent, or Firm*—Ditthavong Mori & Steiner, P.C.

(57) ABSTRACT

The prior art lacks a formulation, application or product of D-Ala7-Angiotensin-(1-7) (A-779) and analogues and derivatives, D-Pro7-Angiotensin-(1-7) and analogues or derivatives or of Ang-(1-7) analogues or derivatives using cyclodextrins, liposomes, biodegradable polymers and its derivatives for the study or treatment of arterial hypertension and other cardiovascular diseases, wounds, burns, arrhythmia, tumors, diabetes mellitus, sperm mobility, nephropathy, gastrointestinal and gynaecologicalgynecological disorders, angiogenesis, angioplatsy, alopecia and blood diseases in warm blooded animals, or as ligands for de G-protein-coupled receptor MAS. This characterizes the present invention as a more effective option for the study and treatment of pathologies associated or not to this receptor. A combination of two different technologies are provided: the molecular encapsulation of the peptide angiotensin-(1-7) and its analogues and derivates in cyclodextrin and the microencapsulation in biodegradable polymers and liposomes. It is also characterized by the increase of this peptides and its analogues and derivatives using the formulation.

25 Claims, No Drawings

SYSTEMS FOR DELIVERY AND RELEASE OF ANGIOTENSIN-(1-7)

This application is the U.S. national phase of international application PCT/BR02/00156 filed in English on 05 Nov. 2002, which designated the U.S. PCT/BR02/00156 claims priority to BR Application No. PI 0105509-7 filed 05 Nov. 2001. The entire contents of these applications are incorporated herein by reference.

FIELD OF THE INVENTION

The present invention is characterized by the process of preparation of formulations of the heptapeptide Angiotensin-(1-7) and its similar ones, agonists and antagonists, using preferentially the cyclodextrins, and derivatives, liposomes, and biodegradable polymers, and/or mixtures of those systems and/or of the derived products. It is also characterized by the identification of the ligand-receptor interaction between the G-coupled receptor, MAS, and angiotensin-(1-7) and its analogues using or not encapsulated formulations, as a target for research and therapeutic interventions in cardiovascular, renal, reproductive, dermatological, tumoral, neurological and blood diseases.

BACKGROUND OF THE INVENTION

In most countries of the world 15% to 25% of the adult population presents high arterial blood pressure (MacMahon S. et. al. Blood pressure, stroke, and coronary heart disease. Lancet 335:765-774, 1990). The cardiovascular risk increases with the level of arterial pressure. The more high the arterial pressure bigger are the risk of cerebral vascular accidents and coronary events. Hypertension, considered the main responsible cause for coronary, cerebral and renal vascular diseases, is the main cause of death and incapability among adults.

The heart failure is worldwide the main cause of hospitalization of patients in the age group of 60 to 80 years old. The aging of the population is already an important factor for the increase in the incidence of heart failure: while 1% of the individuals in the age range of 25 to 54 years old present heart failure, among the more seniors the incidence is very larger, reaching about 10% in those individuals with more than 75 years (Kaannel W. B. et. al. Changing epidemiological features of cardiac failure. Br. Heart J 1994; 72 (suppl): S3-S9).

The heart failure by its clinical characteristic is a restrictive disease, that reduces the quality of the patients' life with its worsening and, in the advanced forms, is characterized as a malign disease with mortality rate above 60% in the first year, even nowadays (Oliveira, M. T. Clinical characteristics and patients' prognostic with advanced congestive heart failure. Faculty of Medicine, USP 1999). It is estimated that these days there are more than 15 million of individuals affected only in the industrialized world and that only in the USA, for example, the number of cases has increased 450% among 1973-1990 (Kannel, W. B. et al. Changing epidemiological features of cardiac failure, Br. Hear J 1994; 72 (suppl 3): S3-S9).

Hypertension is a complex, multifactorial, of high prevalence disease responsible for countless deleterious effects and high morbidity (Kaplan, N. M. Blood pressure the cardiovascular risk factor: prevention ant treatment. JAMA. 275:1571-1576, 1996). Several studies aimed for the evaluation of the effectiveness of its control in the population in general and in special groups have been developed, in order to better understand its course. The control of the normal level of blood pressure without wide intervention with no pharmaceutical drugs of the associated risk factors (such as, diabetes, obesity, smoke) can reduce or even avoid the benefits of the long term treatment of arterial hypertension in the reduction of the mortality, in general, as for coronary disease (Wilson, P. W. et. al. Hypertension, the risk factors and the risk of cardiovascular disease. Raven Press. 94-114).

Hypertension is the pathology that more contributes to the cardiovascular atherosclerosis (The fifth Report of the Joint National Committee on detection, evaluation, and treatment of High Blood Pressure. National Institute of Health (VJNC). Arch. Intern. Med. 153:154-181, 1994). According to statistics, of each four Americans, one is, or will be, hypertensive, and it is estimated 4.78 million people with heart failure. Every year 400 thousand new cases are diagnosed, provoking 800 thousand hospitalizations, with an expense of US$ 17.8 billion of dollars in the treatment.

In Brazil, data from the National System of Health (SUS) show that, in 1997, heart failure was the main cause of hospitalizations among the heart diseases, costing about R$ 150 million for the government in the treatment, corresponding to 4.6% of the whole expense with health (Filho, Albanesi F. Heart failure in Brazil. Arq. Bras. Cardiol, 71:561-562, 1998).

The renin-angiotensin system (RAS) is responsible for the regulation of the arterial pressure, cardiovascular homeostase and hydroelectrolite balance, as in physiological as in pathological conditions (Krieger, E. M.; Santos, R. A. S. Angiotensins—physiologic aspects. Hypertension, 1:7-10, 1998). Angiotensin II (Ang II) is the main peptide of RAS, possessing several actions: vasopressor, stimulator of the synthesis of adrenal steroids, proliferative effect (fibroblasts, smooth muscle of the vasculature) and hypertrophic (cardiomyocytes). Its formation pathways involve the production of angiotensinogen from the liver and renin production in the juxtaglomerular apparatus. Those substances are released in the blood where, the angiotensinogen is hydrolysed by renin, forming Ang I, that, is converted to Ang II, mainly the lung circulation, by the angiotensin converting enzyme (ACE) and it will originate Ang II. This last peptide will act in target-organs distant from the place of its production (Krieger, E. M.; Santos, R. A. S. Angiotensins—physiologic aspects. Hypertension, 1:7-10, 1998).

Recently it was discovered that in parallel to the circulating RAS, that generate Ang II in the circulation, there are independent systems that generates Ang II in different tissues probably for a local action. All the components of the RAS are found in the walls of the blood vessels, in the uterus, in the exocrine portion of the pancreas, eyes, heart, adrenal cortex, testicle, ovaries, anterior and median lobes of the hypophise, pineal and brain. The function of those tissue RAS are not very well understood. (Ardaillou, R.; Michel, J. B. The relative roles of circulating and tissue renin-angiotensin systems. Nephrol. Dial. Transplant., 14:283-286, 1999). The local actions of RAS can occur at the level of the cell that produces the peptide (as an autocrine or intracrine function), or on adjacent cells (as a paracrine function), or in distant sites from the production area (endocrine function).

Recent observations indicate that important peripheral and cerebral actions of the RAS can be mediated by smaller sequences of the angiotensinergic peptides, including Angiotensin-III [Ang-(2-8)], Angiotensin-IV [Ang-(3-8)] and Angiotensin-(1-7). We can consider that both Angiotensin-I [(Ang-(1-10)] and Angiotensin-II [Ang-1-8)] can suffer a biotransformation process, generating a whole "family" of biological active angiotensin peptides. (Santos, R. A. S.;

Campagnole-Santos, M. J.; Andrade, S. P. Angiotensin-(1-7): an update. Regulatory Peptides, 91:45-62, 2000).

Angiotensin-(1-7) is a biologically active peptides of the angiotensin "family", being formed by a pathway independent of the ACE. Ang I processing by endopeptidases or Ang II by prolyl-peptidases or carboxy-peptidases can generate the heptapeptide, Ang-(1-7). Ang-(1-7) can be hydrolysed by amino-peptidases generating Ang-(2-7) and Ang-(3-7). The hydrolysis of Ang-(1-7) by ACE originates Ang-(1-5) (Santos, R. A. S.; Campagnole-Santos, M. J.; Andrade, S. P. Angiotensin-(1-7): an update. Regulatory Peptides, 91:45-62, 2000).

Ang-(1-7) and Ang II are the main efectors of the RAS. However, two important characteristics differentiate Ang-(1-7) from Ang II: the first one possesses highly specific biological actions and its formation pathway is independent of ACE (Santos, R. A. S.; Campagnole-Santos, M. J.; Andrade, S. P. Angiotensin-(1-7): an update. Regulatory Peptides, 91:45-62, 2000).

The primary objective of hypertension treatment not only seeks for the fall expenses, but as well as the prevention of end-organ damages, through modifications of life quality and the use of medications, when necessary (The Fifth Report of The Joint National Committee on detection, evaluation, and treatment of High Blood Pressure. National Institute of Health (VJNC). Arch. Intern. Med. 153:154-181, 1994).

The use of anti-hypertensive drugs is indicated when patients do not respond to the alterations in lifestyle for a period of three to six months, and in the presence of end-organs damage (left ventricular hypertrophy, myocardic ischemia, stroke, or hypertensive retinopathy). All patients with systolic arterial pressure above 180 mmHg or diastolic arterial pressure above 110 mmHg should be submitted to pharmacological treatment, independent of the presence of another (Report the Canadian Hypertension Society. Consensus Conference. 3. Pharmacological treatment of essential hypertension. Xan. Med. Assoc. J. 149 (3): 575-584, 1993).

During the years 70 and 80, however, the anti-hypertensives became an important tool for the treatment of the high arterial pressure (Ménard, J. Anthology of renin-angiotensin system: The one hundred reference approach to angiotensin antagonist II. J. Hypertension 11 (suppl 3): S3-S11, 1993). During the last four decades, the pharmacological research produced new classes of drugs to treat the hypertension: the diuretics in the sixties, the beta-blockers in the seventies, the calcium channel blockers, the angiotensin II antagonists and the ACE in inhibitors.

The diuretics can be divided in three categories: thazidics, loop diuretics and the potassium savers. The thazidics and analogues include chlorothiazides and hydroclorotiazidehydroclorotiazide, which induce in the first days of treatment a 10-15% of decrease in the arterial pressure mainly due to a decrease in the extracellular volume and an increase in the diuresis and natriuresis. After six months, the blood volume and cardiac output return to baseline levels and the decrease in arterial pressure is maintained by a decrease in peripheral vascular resistance (Frolich, E. Current Approaches in the treatment of Hypertension, 405-469). These drugs are habitually used as monotherapy and the give best results in black patients and, at low doses, in the old patients. They have as collateral effects: increase in peripheral resistance to insulin, increase in triglicerides levels, increase in LDL, hypocalcemia, hyperucemia. Among the loop diuretics are furosemide, bumetamide and trianterene, and they are much more potent than the thiazides. They act predominantly in the medullar and cortical portions of the Henle loop. They present the same collateral effects of the thiazides. The potassium savers, however, which include amolonide, trianterene and speronolactones are drugs with weak diuretic action and rarely used alone.

The betablockers, such as Atenolol and Nadolol, are classified in beta-1 and beta-2 and the mechanism of action are not completely defined. They present as collateral effects: alteration in the response to insulin, prolongation of the hypoglicemichypoglycemic coma, increase in triglicerides levels and increase in creatinine due to a decrease in renal flow.

The calcium channel blockers are being used for at least 25 years (Frolich, E. D. Current Approaches in the Treatment of Hypertension, 405-469, 1994). They can be classified in two major groups, according to its pharmacological actions: those that have larger action in the conduction of the stimulus, such as Verapamil and Diltiazem, and those that present a predominant vasodilator action, as those derived from diidropirinicos (Nifedipine and others) (Frolich, E. D., Hypertension. Adult Clinical Cardiology Self Assessment Program (ACCSAP), 6: 3-19, 1995). They present as collateral effects edema of inferior members and tachycardia.

The main action of the ACE inhibitors is to inhibit the conversion of angiotensin I in to angiotensin II. Thus, the essentially vasoconstrictor actions of angiotensin II are minimized. Teprotide, the first ACE inhibitor clinically used, exerted its anti-hypertensive action only when it was administered by intravenous route, because it was inactive when given orally, what have limited its employment. It is known now that ACE is an enzyme with multiple actions, i.e., that it acts in several substrate. Besides acting as a dipeptidase in the angiotensin I and in the bradykinin, it is also capable of hydrolysing peptidic chains of the natriuretic peptide, indicating that the enzyme can act in several tissues. ACE has an important role in the inactivation of circulating and tissue Ang-(1-7). The circulating concentration of this peptide is similar to Ang II concentration and it has been shown that it increases after inhibition of ACE. This increase can be due to both the increase in its precursor (Ang I) and the decrease in its degradation by ACE (Santos, R. A. S.; Campagnole-Santos, M. J.; Andrade, S. P. Angiotensin-(1-7): an update. Regulatory Peptides, 91:45-62, 2000). The ACE inhibitors are excellent when administered as monotherapy, since they induce a relatively fast fall in arterial pressure in 60 to 70% hypertensive patients. (Ganong, W. Neuropeptides in cardiovascular control. J. Hypertens 2 (suppl 3): 15-22, 1984). In addition, they are in general well tolerated, but its use can cause collateral effects and adverse reactions, some of which are relatively serious, among them angiodema, cutaneous eruptions and dry coughs (8 to 10%).

The first attempts to develop Ang II antagonists are from the beginning of the 70's decade and they were concentrated on the development of peptides similar to Ang II. The first antagonist was saralasina, 1-sarcosina, 8-isoleucina angiotensin II, that was followed by others. However, they did not have clinical acceptance, because they presented partial agonist activity. In 1982 were developed the first two selective antagonists for the $AT_1$ receptor of non-peptidic characteristic (S-8307 and S8308). However, eventhough they were highly specific and without agonist activity, they presented a weak bind to Ang II'S receptors. With a series of modifications in the molecular structure of those two precursors, to improve the potency and to retain the selectivity and to reach the pharmacokinetis properties, a new product of orally active, potent and of high specificity was developed, Losartan. Starting from then, many other antagonists of non-peptidic origin were developed, such as Candesartan, Irbesartan, Valsartan, Telmisartan, Eprosartan, Tasosartan and Zolasartan.

Angiotensin-(1-7), (Asp-Arg-Val-Tyr-Ile-His-Pro) (SEQ ID NO:1) and its derivative one [Sar[1]]-Ang-(1-7) antagonize Ang II pressor effect in man (Ueda S, Masumori-Maemoto S, Ashino K, Nagahara T, Gotoh and, Umemura S, Ishii M. Angiotensin-(1-7) attenuates vasoconstriction evoked by angiotensin II but not by noradrenaline in man. Hypertension 2000; 35:998-1001) and mice (Bovy P R, Trapani A J, McMahon E G, Palomo M. The carboxy-terminus truncated analogue of angiotensin II [Sar[1]]-angiotensin II-(1-7)-amide, provides an entry to the new class of angiotensin II antagonists. J Med Chem. 1989; 32:520-522). The contraction produced by Ang II in isolated arteries of rabbits and humans is also reduced by angiotensin-(1-7) (Bovy P R, Trapani A J, McMahon E G, Palomo M. The carboxy-terminus truncated analogue of angiotensin II [Sar[1]] angiotensin II-(1-7)-amide, provides an entry to the new class of angiotensin II antagonists. J Med Chem. 1989; 32:520-522. Roks A J, Van-Geel P P, Pinto Y M, Buikema H, Henning R H, of Zeeuw D, van-Gust W H. Angiotensin-(1-7) is a modulator of the human renin-angiotensin system. Hypertension 1999; 34(2): 296-301).

Until very recently, the receptor(s) responsible for the transduction of the Ang-(1-7) response had not been identified and many possibilities were raised regarding Ang-(17) signal transduction. The first evidence for the existence of different receptors and/or different mechanisms of signal transduction for Ang-(1-7) effects was based on the demonstration that several Ang-(1-7) actions are different and even opposite from those ascribed for Ang II. Recently, the heptapeptide D-[Ala[7]]-Ang-(1-7) (A-779) was characterized as a potent antagonist for Ang-(1-7) effects (Santos R A S, Campagnole-Santos M J, Baracho N C V, Fontes M A P, Silva L C S, Neves L A A, Oliveira D R, Caligiorne S M, Rodrigues A R V, Gropen Jr. C, Carvalho W S, Silva A C S, Khosla M C. Characterization of the new angiotensin antagonist selective goes angiotensin-(1-7): Evidence that the actions of angiotensin-(1-7) it plows mediated by specific angiotensin receptors. Brain Res. Bull. 1994; 35:293-299). The results of that study indicated that this analogue is a selective antagonist of Ang-(1-7) without demonstrating agonist activity in several biological preparations. A-779 was shown to potently antagonize the antidiuretic effect of Ang-(1-7) in rats with water overload. The vasodilatation produced by Ang-(1-7) in the afferent arterioles of rabbits, the Ang-(1-7) pressor effect in the RVLM, the vasodilation produced in the mesenteric microcirculation in vivo are completely blocked by the administration of A-779, and are not affected by the selective Ang II antagonists. Other studies using bovine endothelial cells, dog coronary arteries, SHR aorta, human epithelial fibroblasts, human heart fibroblasts and kidney slices have supported the evidences for the existence of specific receptors of Ang-(1-7) that can be blocked by the A-779. (Santos, R A S; Campagnole-Santos, M J.; Andrade, S P. Angiotensin-(1-7): an update. Regulatory Peptides, 91:45-62, 2000).

A-779 and its analogues such as Sar1-D-Ala 7-Ang-(1-7) (Bovy P R, Trapani A J, McMahon E G, Palomo M. THE carboxy-terminus truncated analogue of angiotensin II [Sar1] angiotensin II-(1-7)-amide, provides an entry to the new class of angiotensin II antagonists. J Med Chem. 1989; 32:520-522.), and the D-Pro7-Ang-(1-7) (Naves-Santos, V., Khosla, M. C., Oliveira, R. C., Campagnole-Santos, M. J., Lima, D. X., Santos, R A S. Selective inhibition of the effect central pressor of angiotensin-(1-7) for its similar one [D-Pro7]-angiotensin-(1-7). XI Reunião Annual of the Federation of Society of Experimental Biology, 1996, Caxambu, M G) and others can serve extremely as tools to elucidate biological effects of Ang-(1-7).

It has been demonstrated that Ang-(1-7) acts inside the RAS as a contraregulatory peptide of this system, acting at multiple points (Ferrario C M, Chappell M C, Dean R H, Iyer S N. Novel angiotensin peptides regulate blood pressure, endothelial function, and natriuresis. J Am Soc Nephrol. 1998; 9: 1716-1722. Santos, R. Campagnole-Santos, M J, Andrade, S P. Angiotensin-(1-7): an update. Regulatory Peptides, 91:45-62, 2000. Heringer-Walther S, Batista E N, Walther T, Khosla M C, Santos R A S, Campagnole-Santos M J. Baroreflex improvement in SHR after ACE inhibitors involves angiotensin-(1-7). Hypertension, 37: 1309-1313, 2001).

Ang-(1-7) decreases angiogenesis and cellular proliferation (Machado, R D P, Santos, R A S, Andrade, S P. Mechanisms of angiotensin-(1-7) induced inhibition of angiogenesis. Am J Physiol, 280: 994-1000, 2001. Rodgers K, Xiong S, Félix J, Rotates N, Espinoza T, Maldonado S, Dizerega G. Development of angiotensin-(1-7) the in the agent to acelerate dermal repair. Wound Repair Regen, 9: 238-247, 2001) presenting therefore a potential for the treatment of lesions. Ang-(1-7) can act as an ACE inhibitor in the amino-terminal domain of the enzyme, in which it acts as substrate, as well in the c-terminal domain in which it acts as an inhibitor (Deddish P A, Marcic B, Jackman H L, Wang H Z, Skidgel R A, Erdös E G. N-domain-specific substrate and C-domain inhibitors of angiotensin-converting enzyme: angiotensin-(1-7) and keto-ACE. Hypertension. 1998; 31:912-917. Tom B, Of Vries R, Saxena P R, Danser A H J. Bradykinin potentiation by angiotensin-(1-7) and ACE inhibitors correlates with ACE C- and N-domain blockade. Hypertension, 38: 95-99, 2001). Its IC50 for inhibition of ACE is approximately 1 micromolar (Chappell M C, Pirro N T, Sykes T H E, Ferrario C M. Metabolism of angiotensin-(1-7) by angiotensin-converting enzyme. Hypertension. 1998; 31(part 2): 362-367. Paula, R D, Lima, C V, Britto, R R, Campagnole-Santos, M J, Khosla, M C, Santos, R A S. Potentiation of the hypotensive effect of bradykinin by angiotensin-(1-7)-related peptides. Peptides, 20:493-500, 1999. Deddish P A, Marcic B, Jackman H L, Wang H Z, Skidgel R A, Erdos E G. N-domain-specific substrate and C-domain inhibitors of angiotensin-converting enzyme: angiotensin-(1-7) and keto-ACE. Hypertension, 31:912-917, 1998).

In addition to the ACE inhibitory activity, Ang-(1-7) inhibits the Ang II actions by two different mechanisms: 1) competing for the ligation on $AT_1$ receptors (Bovy P R, Trapani A J, McMahon E G, Palomo M. The carboxy-terminus truncated analogue of angiotensin II [Sar[1]]-agiotensin II-(1-7)-amide, provides an entry to the new class of angiotensin II antagonists. J Med Chem. 1989; 32:520-522.—Ueda S, Masumori-Maemoto S, Ashino K, Nagahara T, Gotoh A N D, Umemura S, Ishii M. Angiotensin-(1-7) attenuates vasoconstriction evoked by angiotensin II but not by noradrenaline in man. Hypertension 2000; 35:998-1001. Roks A J, Van-Geel P P, Pinto Y M, Buikema H, Henning R H, deZeeuw D, van-Gilst W H. Angiotensin-(1-7) is a modulator of the human renin-angiotensin system. Hypertension 1999; 34(2): 296-301. Rowe B P, Saylor D L, Speth R C, Absher D R. Angiotensin-(1-7) binding at angiotensin II receptors in the rat brain. Regul Pep. 1995; 56(2): 139-146. Mahon J M, Carrr R D, Nicol A K, Hendersn I W. Angiotensin-(1-7) is an antagonist at the type 1 angiotensin II receptor. J Hypertension 1994; 12:1377-1381), and 2) altering the signalling mechanisms of Ang II effects, possibly by altering the availability of intracellular calcium (Chansel D, Vandermeerch S, Andrzej T, Curat C, Ardaillou R. Effects of angiotensin IV and angiotensin-(1-7) on basal angiotensin II-stimulated cytosolic $Ca+2$ in mesangial cells. Eur J Pharmacol. 2001; 414:165-

175). A third mechanism for which Ang-(1-7) can antagonize the Ang II deleterious effects on the cardiovascular system are the potentiation of the bradykinin effects (Paula, R D; It Rasps, C V, Khosla, M C, Santos, R A S. Angiotensin-(1-7) potentiates the hypotensive effect of bradykinin in concious rats. Hypertension, 26: 1154-1159, 1995. Li P, Chappell M C, Ferrario C M, Brosnihan K B. Angiotensin-(1-7) augments bradykinin-induced vasodilation by competing with ACE and releasing nitric oxide. Hypertension. 1997; 29 (part 2): 394-400).

Bradykinin is an endogenous peptide with potent vasodilatatory action (Rocha and Silva, M, Beraldo, W T, Rosenfeld, G. Bradykinin, the hypotensive and smooth muscle stimulating factor releases from shapes globulin by snake venoms and by trypsin. Am. J. Physiol. 156, 261-273, 1949). It has also been described beneficial actions of bradykinin in the heart (Linz W, Wohlfart P, Scholkens B A, Malinski T, Wiemer G. Interactions among ACE, kinins and NO. Cardiovasc Res. 1999; 43:549-561). Ang-(1-7) potentiate the effects of bradykinin, in vessels (Paula, R. D.; Lima, C. V.; Khosla, M. C.; Santos, R. A. S. Angiotensin-(1-7) potentiates the hypotensive ffect of bradykinin in concious rats. Hypertension, 26: 1154-1159, 1995. Li P, Chappell M C, Ferrario C M, Brosnihan K B. Angiotensin-(1-7) augments bradykinin-induced vasodilation by competing with ACE and releasing nitric oxide. Hypertension. 1997; 29 (part 2): 394-400), in the heart (Almeida, A P, Frábregas, B C, Madureira, M M, Santos, R J S, Campagnole-Santos, M J, Santos, R A S. Angiotensin-(1-7) potentiates the coronary vasodilatory effect of bradykinin in the isolated rat heart. Braz. J. of Medical and Biological Research, 33: 709-713, 2000).

A particular drug could be chemically modified in order to alter its properties such as biodistribution, pharmacokinetics and solubility. Various methods have been used to increase the solubility and stability of drugs, among them the use of organic solvents, their incorporation within emulsions or liposomes, the adjustment of pH, their chemical modifications and their complexation with the cyclodextrins.

The cyclodextrins are oligosaccharides cyclic family, which include six, seven or eight units of glucopyranose. Due to sterics interactions, the cyclodextrins, CD's, form a cycle structure in the shape of a (cone truncado) with an internal cavity apolar. Those are compounds chemically stable that can be modified in a regioselective way. The cyclodextrins hosts form complexes with various hydrophobic guests in their cavity. The CD's have been used for the solubilization and encapsulation of the drugs, perfumes and fragrances as described by Szejtli, J., Chemical Reviews, (1998), 98, 1743-1753. Szejtli, J., J. Mater. Chem., (1997), 7, 575-587.

According to detailed studies of toxicity, mutagenecity, teratogenecity and carcinogenecity about the cyclodextrins, described in [Rajewski, R. A., Stella, V., J. Pharmaceutical Sciences, (1996), 85, 1142-1169], these are presented with low toxicity specially of the (hydroxypropyl-β-cyclodextrin, as reported in Szejtli, J. Cyclodextrins: properties and applications. Drug investing., 2(suppl. 4): 11-21, 1990. Except for some high concentrations of some derivates which cause harm to the erythrocytes, these products in general are not harmful to the health. The use of cyclodextrins as additives in foods has already been authorized in countries such as Japan and Hungary, and for more specific applications, in France and Denmark. Besides this, they are obtained from a renewable source of degradation of the amide. All these characteristics are a high motivation for the research findings of new applications. The structure of the molecule of CD is similar to a cone truncate one, of Cn approximately symmetry. The primary hydroxilas are located in the narrowest side of the cone by the intramolecular hydrogen bonds, this element is flexible enough to allow a considerable deviance in the regular shape.

The known cyclodextrin derivatives can be classified according to their polarity, size, biological activity, etc. As for their practical uses are classified as follows: 1. Carriers (solubilizers, stabilizers) for biologically active substances; 2. Enzyme models; 3. Separating agents (for chromatography or batch-processes); 4. Catalysts and additives (as detergents, viscosity modifiers, etc), L. Szente and J. Szejtli, Adv. Drug Deliv. Rev. 36 (1999), 17. The CD's are moderately soluble in water, methanol and ethanol and readily soluble in polar solvents, such as the dimethyl sulfoxide, dimethyl formamide, N,N-dimethyl acetamide e piridine.

Numerous research works exist in the literature about the effects of the increase of solubility in water of the guests little soluble in water, using the cyclodextrins through the using compounds of inclusion were describe in Szejtli, J., Chemical Reviews, (1998), 98, 1743-1753. Szejtli, J., J. Mater. Chem., (1997), 7, 575-587.

In order to design a drug delivery system (DDS) various kinds of high performance carrier materials are being developed to deliver the necessary amount of drug to the targeted site for a necessary period of time, both efficiently and precisely. Cyclodextrins, biodegradable or non biodegradable polymers, liposomes, emulsions, multiple emulsions are potential candidates for such a role, because of their ability to alter physical, chemical, and biological properties of guest molecules Besides the cyclodextrins, a number of drug delivery systems have been investigated, including polymer microcapsules, microparticles, liposomes and emulsion. Many of these are prepared from synthetic biodegradable polymers such as polyanhydrides and poly(hydroxy acids). In these systems the drugs incorporate in a polymeric microspheres, which release the drug inside the organism, in small and controlled daily doses, during days, months or until years.

Several polymers already were tested in controlled release systems. Such as: polyuretans for its elasticity, polysiloxans or silicons for being a good one insulating, polymethyl-methacrilate for its physical force, polyvinyl alcohol for its hydrophobicity and resistance, polyethylene for its hardness and impermeability (Gilding, D. K. Biodegradable polymers. Biocompat. Clin. Impl. Mater. 2:209-232, 1981). Biodegradable polymers and biocompatible polymers, hve been extensively investigated as vehicle for controlled release systems due to their ability to undergo surface degradation. These kind of polymers can be chose from: poly(hydroxy-ethylmethacrylate), polyacrylamide, polymer from lactic acid (PLA), from glicolic acid (PGA), and the respective ones co-polymers, (PLGA) and the poly(anidridesanhydrides), as described by Tamada and Langer, J. Biomater. Sci. Polym. Edn, 3(4): 315-353.

A formulation of the present invention can also include other components such as a pharmaceutical acceptable excipient. For example, formulation of the present invention can be formulated in an excipient that the animal to be protected can tolerate. Excipients can also contain minor amounts of additives, such as substances that enhance isotonicity and chemical stability of buffers. Standard formulation can either be liquid injectables or solids which can be taken up in a suitable liquid as a suspension or solution for injection or oral formulation. Suitable controlled release vehicles include, but are not limited to, biocompatible polymers, other polymeric matrices, capsules, microcapsules, nanocapsules, microparticles, nanoparticles, bolus preparations, osmotic pumps, diffusion devices, liposomes, lipospheres and transdermal delivery systems, implantable or not.

In the last years, several systems of drugs delivery systems have been studied to improve the drug absorption, to increase the drug stability and target it to a certain cell population. These studies led to the development of several products based on cyclodextrins, emulsions, liposomes and polymers for drug carrying and delivering. These formulations can be administered through intramuscular, intravenous, subcutaneous injection, oral application, inhalation or devices that can be implanted.

Liposomes are lipid vesicles that include aqueous internal compartments in which molecules, for example drugs, are encapsulated with the objective of reaching a controlled release of the drug after administration in individuals.

Many different techniques have been proposed for the preparation of liposomes [U.S. Pat. No. 4,552,803, Lenk; U.S. Pat. No. 4,310,506, Baldeschwieler; U.S. Pat. No. 4,235,871, Papahadjopoulos; U.S. Pat. No. 4,224,179, Schneider; U.S. Pat. No. 4,078,052, Papahadjopoulos; U.S. Pat. No. 4,394,372, Tailor; U.S. Pat. No. 4,308,166, Marchetti; U.S. Pat. No. 4,485,054, Mezei; and U.S. Pat. No. 4,508,703, Redziniak; Woodle and Papahadjopoulos, Methods Enzymol. 171:193-215 (1989)]. Unilamellar vesicles display a single membrane [Huang, Biochemistry 8:334-352 (1969)] while multilamellar vesicles (MLVs) have numerous concentric membranes [Bangham et al., J. Mol. Biol. 13:238-252 (1965)]. The procedure of Bangham [J. Mol. Biol. 13:238-252 (1965)] produces "ordinary MLVs", that present unequal solute distributions among the aqueous compartments and, consequently, differences of osmotic pressure. Lenk et al. (U.S. Pat. No. 4,522,803; U.S. Pat. No. 5,030,453 and U.S. Pat. No. 5,169,637), Fountain et al. (U.S. Pat. No. 4,588,578), Cullis et al. (U.S. Pat. No. 4,975,282) and Gregoriadis et al. (Pat. W.O. 99/65465) introduced methods for the preparation of MLVs that present substantially equal solute distributions among the compartments. Similar solute distributions among the different compartments mean a larger drug encapsulation efficiency as well as smaller differences of osmotic pressure that turns these MLVs more stable than ordinary MLVs. Unilamellar vesicles can be produced by sonication of MLVs [Papahadjopoulos et al. (1968)] or by extrusion through polycarbonate membranes [Cullis et al. (U.S. Pat. No. 5,008,050) and Loughrey et al. (U.S. Pat. No. 5,059,421)].

Satisfactory lipids include for example, phosphatidylcholine, phosphatidylserine, phosphatidylglycerol, cardiolipin, cholesterol, phosphatidic acid, sphingolipids, glycolipids, fatty acids, sterols, phosphatidylethanolamine, polymerizable lipids in their polymerized or non-polymerized form, mixture of these lipids.

The composition of the liposomes can be manipulated such as to turn them specific for an organ or a cell type. The targeting of liposomes has been classified either on the basis of anatomical factors or on the basis of the mechanism of their interaction with the environment. The anatomical classification is based on their level of selectivity, for example, organ-specific or cell-specific. From the point of view of the mechanisms, the targeting can be considered as passive or active.

The passive targeting exploits the natural tendency of conventional liposomes to be captured by the cells of the reticuloendothelial system, i.e. mainly the fixed macrophages in the liver, spleen and bone marrow. Sterically stabilized liposomes (also well-known as "PEG-liposomes") are characterized by a reduced rate of elimination from the blood circulation [Lasic and Martin, Stealth Liposomes, CRC Press, Inc., Boca Raton, Fla. (1995)]. PEG-liposomes present a polyethylene glycol polymer conjugated to the head group of some phospholipid that reduces their interaction with plasma proteins, such as opsonins, and reduces the rate of their uptake by cells. The resulting steric barrier allows these liposomes to remain for a longer period of time within the circulation than conventional liposomes [Lasic and Martin, Stealth Liposomes, CRC Press, Inc., Boca Raton, Fla. (1995); Woodle et al., Biochim. Biophys. Acta 1105:193-200 (1992); Litzinger et al., Biochim. Biophys. Acta 1190:99-107 (1994); Bedu Addo, et al., Pharm. Res. 13:718-724 (1996)]. The drug encapsulation within PEG-liposomes has resulted in the improvement of the effectiveness of many chemotherapeutic agents [Lasic and Martin, Stealth liposomes, CRC Press, Inc., Boca Raton, Fla. (1995)] and bioactive peptides [Allen T. M. In: Liposomes, New Systems, New Trends in their Applications (F. Puisieux, P. Couvreur, J. Delattre, J. -P. Devissaguet Ed.), Editions de la Santé, France, 1995, pp. 125].

Studies in this area demonstrated that different factors affect the effectiveness of PEG-liposomes. Ideally, the diameter of the vesicles should be below 200 nm, the number of units in PEG of approximately 2.000 and the proportion of Pegylated lipid from 3 to 5 mol % [Lasic and Martin, Stealth Liposomes, CRC Press, Inc., Boca Raton, Fla. (1995); Woodle et al., Biochim. Biophys. Acta 1105:193-200 (1992); Litzinger et al., Biochim. Biophys. Acta 1190:99-107 (1994); Bedu Addo et al., Pharm. Res. 13:718-724 (1996)].

The active targeting involves alteration of liposomes through their association with a ligand, such as a monoclonal antibody, a sugar, a glycolipid, protein, a polymer or by changing the lipid composition or the liposome size to target them to organs and cells different from those which accumulate conventional liposomes.

Liposome-based vehicles have been proposed for a large variety of pharmacologically active substances, including antibiotics, hormones and antitumoral agents [Medical applications of liposomes (D. D. Lasic, D. Papahadjopoulos Ed.), Elsevier Science B. V., Holland, 1998].

Ang-(1-7) and its analogues have great potential for study and treatment of several diseases including cardiovascular disorders. Another important aspect related RAS is related to the clear need of amplification of the knowledge about its physiologic actions that can propitiate the development of new therapeutic strategies. However, the conventional way of administration of most of the drugs anti-hypertensive especially biologically active peptides, as the angiotensins and derivatives, suffers limitations due to the short half-life of peptides.

In that sense, the present invention is characterized by the use of liposomes, cyclodextrins and biodegradable polymers as controlled release systems of the angiotensins and derivatives to increase their bioavailability, the duration and intensity of their biological effects.

The formulation of the present invention is characterized by the use of the mixture of excipients pharmaceutically acceptable for Ang-(1-7) and/or analogues. Excipients examples include water, saline solution, buffered phosphate solutions, the solution of Ringer, dextrose solution, the solution of Hank, biocompatible saline solutions with or without polyethylene glycol. Non aqueous vehicles, as fixed oils, sesame oil, ethyl-oleate, or triglicerides can also be used. Other useful formulations include agents capable to increase the viscosity, as carboxymetilcelulose of sodium, sorbitol, or dextran The excipients can also contain smaller amounts of additives, such as substances that increase isotonicity and chemical stability of substance or buffers. Examples of buffers include phosphate buffer, bicarbonate buffer and Tris buffer, while examples of preservatives include timerosal, m- or o-cresol, formalin and benzyl-alcohol. The formulation state can be liquid or solid. In the case of a non-liquid formulation, the excipients can include dextrose, human serum albumin, preservatives, etc. for which water or sterile saline solution can be added before the administration.

The present invention is also characterized by the preparation of controlled release systems containings Ang-(1-7) and/or its analogues for interaction ligand-receptor with the G Protein-coupled receptor, MAS. Satisfactory systems of controlled release include, but are not limited to, the ciclodextrinescyclodextrins, biocompatible polymers, biodegradable polymers, other polymeric matrixes, capsules, micro-capsules, microparticles, bolus preparations, osmotic pumps, diffusion devices, liposomes, liposferes, and systems of transdermic administration. Other compositions of controlled release of the present invention include liquids that, when submitted the temperature changes, form a solid or a gel in situ.

The MAS receptor (Young, D., Waitches, G., Birchmeier, C., Fasano, O., and Wigler, M. (1986). Isolation and characterization of a new cellular oncogene encoding a protein with multiple potential transmembrane domains. Cell 45: 711-719) was initially described as an angiotensin II receptor (Jackson, T. R., Blair, A. C., Marshall, J., Goedert, M. & Hanley, M. R. The MAS oncogene encodes an angiotensin receptor. Nature 335, 437-440 (1988)), however subsequent studies showed that this hypothesis was not right (Ambroz, C., Clark, A. J. L. & Catt, K. J. The MAS oncogene enhances angiotensin-induced [Ca2+]i responses in cells with pre-existing angiotensin II receptors. Biochem. Biophys. Acta 1133, 107-111 (1991)). This protein is expressed in the brain (Bunnemann, B., Fuxe, K., Metzger, R., Mullins, J., Jackson, T. R., Hanley, M. R. & Ganten, D. Autoradiographic localization of MAS proto-oncogene mRNA in adult rat brain using in situ hybridization. Neurosci. Lett. 114, 147-153 (1990)) and in other tissues. There is no description in the literature of an interaction of MAS with angiotensin-(1-7) or its analogues.

The present invention is characterized by the obtention of systems of controlled release of the heptapeptide Angiotensin-(1-7) and/or its derivatives, using the cyclodextrins and/or its derivatives, that decrease the degradation of the peptide in the treatment gastrointestinal (TGI), meaning larger biodisponibility of the peptide in the biological system. The present invention it is characterized by the obtention of controlled release systems of the heptapeptide Angiotensin-(1-7) and/or of its analogues, using biodegradable polymers, liposomes or mixtures of those systems with cyclodextrins, which increase the biodisponibility of the peptides.

Until the present, any application using the heptapeptide Angiotensin-(1-7) or its analogues, agonists and antagonists associated to the cyclodextrins or theirs derivatives, to biodegradable polymers or to liposomes, was not described.

The present invention can be understood better through the following examples:

EXAMPLE 1

This example describes the preparation of Ang-(1-7) in the encapsulated form in sterically stabilized liposomes and the improvement of the bioavailability of Ang-(1-7) when administered in that form.

The encapsulation of Ang-(1-7) in liposomes was performed according to Kirby and Gregoriadis [Biotechnology 2:979-984 (1984)] and was followed by the extrusion of the liposome suspension through polycarbonate membranes with a pore size of 200 nm [Nayar et al. Biochim. Biophys. Acta. 986:200-206 (1989)]. Peptide-containing liposomes were then separated from non-encapsulated peptide by dialysis and finally sterilized by filtration through sterile membranes of 0.22 micrometers. A lipid composition of distearoyl-phosphatidylcholine, cholesterol and distearoyl-phosphatidylethanolamine-polyethylene glycol (2,000), at a molar ratio of 5:4:0.3, was chosen. The amount of encapsulated peptide was determined using the intrinsic fluorescence of Ang-(1-7). Encapsulation was achieved with an efficiency of 12% and a peptide/lipid ratio of 0.03 (p/p). The size of liposomes was determined through the dynamic light scattering technique. A mean vesicle diameter of 0.19 micrometer was determined.

Ang-(1-7)-containing liposomes (LAng) were unilaterally microinjected (35 ng of Ang-(1-7) in 200 nL) in the rostro-ventrolateral medulla (RVLM) of Wistar rats with a needle (30 G) that was inserted slowly in the brain. Empty liposomes (LEmp) were also similarly microinjected at the same lipid dose. The mean arterial blood pressure (MAP) was determined by telemetry 4 days before and 12 days after microinjection in freely moving undisturbed animals.

The microinjection of LAng produced a significant pressor effect during day-time that was maintained for 5 days. The highest MAP was obtained on day 3 (114±4 mmHg) that differed significantly from that registered on day 0 (100±3 mmHg). As expected, LEmp did not produce significant alteration of MAP (94±5 mmHg in 3 vs 90±5 mmHg in 0). Moreover, day-time MAP was significantly higher in LAng group than in Lemp group on day 1, 2 and 3. Night-time MAP, in contrast to day-time MAP, was not affected significantly by the microinjection of LAng.

Previous studies established that microinjection of free Ang-(1-7) (not encapsulated) in the RVLM, at a similar dose (25-50 ng), produced a 15 mmHg increase of PAM for approximately 10 min. The short duration of this effect was attributed to the elevated metabolism of the peptide in the free form. Therefore, the present technology established, in chronic conditions, the pressor effect of Ang-(1-7) at the level of RVLM. It is also characterized by the capacity to increase the bioavailability of the peptide.

EXAMPLE 2

Preparation of the microspheres in the basis of biodegradable polymer (PLGA) of Ang-(1-7) for the controlled release of the peptide.

Firstly a emulsion constituted of an organic phase constituted of poly(acid lactic-glycolic) (PLGA) dissolved in dichloromethane and an aqueous phase constituted of the 1.8 mg of Ang-(1-7). That emulsion is then submitted to the sonication for half minute and is added to 1% (PVA) solution, forming a second emulsion, which suffers stirring for 1 minute to complete homogenization of the microemulsion. The system is maintained under stirring without heating, for 2 hours until the evaporation of the solvent. The mixture is centrifuged by 2 to 3 times, and washed three times with water to remove the surface-adsorbed PVA and finally resuspended in 2 mL of water and freeze-dried. Then the solid microspheres were characterized through the thermal analysis and scanning electron microscopy SEM. The microspheres DSC curve shown a vitreous transition similar to which it was observed to the PLGA polymer. The respectively SEM micrographs shown 50 microns of particles size. It is still verified the porous surface of the microspheres. To determine the peptide encapsulation was accomplished by radioimmunoassay [Neves et al., Biochem. Pharmacol. 50:1451-1459 (1995)]. It was obtained 15% of peptide encapsulation. The kinetics profile shown the 60% of peptide release approximately in 8 h and about 90% in 48 h.

EXAMPLE 3

Preparation of the Inclusion Compounds between β-cyclodextrin and Ang-(1-7).

The preparation is made in equimolar proportions of cyclodextrin and Ang-(1-7). In briefly, β-cyclodextrin and/or its derivatives is dissolved in water using stirring and heating. Then the respective amount of angiotensin-(1-7) is added to the aqueous solution. Following the dissolution, the mixture is frozen in liquid nitrogen and submitted tc the lyophilization process, obtaining a dry solid. The solid obtained is then submitted to the physical-chemistry characterization using the FT infrared spectroscopy, thermal analysis (TG/DTG and DSC), X-ray diffraction and 1 H and 13 C NMR spectroscopy and T1 relaxation times.

EXAMPLE 4

This example describes the identification of an interaction between angiotensin-(1-7) and its analogues with the G protein-coupled receptor, MAS.

Angiotensin-(1-7) labeled with 125I or rhodamine-angiotensin-(1-7), fluorescent, were incubated with mouse kidney slices from normal or MAS knockout animals. After incubation for variable intervals at 4oC the slices were exposed to autoradioghraphic films or analysed by flourescent microscopy. In the knockout mice the specif binding for angiotensin-(1-7) disappeared while the binding for Ang II or Ang IV, used as controls, was inaltered. The Ang_(1-7) binding in kidney slices of wild type mice was displaced by the analogues D-Ala$^7$-Angiotensin-(1-7) e D-Pro$^7$-Angiotensin-(1-7). The functional test for the absence of binding in knockout mice was made using the water diuresis model (administration of 5% of the body weight, of H$_2$O). Ang-(1-7) treatment (4 pmol/10 g BW) in wild type mice produced a reduction of the urine volume (antidiuresis). In MAS knockout mice the antidiuretic effect of Ang-(1-7) was absent.

3. The formulation of claim 1, wherein said hydrophilic cyclodextrin is an alpha-, beta- or gamma-cyclodextrin.

4. The pharmaceutical formulation of claim 1, wherein the hydrophilic cyclodextrin is a member selected from the group comprising 6-O-maltosyl-, -cyclodextrin, sulfobutyl-, -cyclodextrin, 2-hydroxyethyl cyclodextrin, 2-hydroxypropyl cyclodextrin, 3-hydroxypropyl cyclodextrin, and 2,3-dihydroxypropyl cyclodextrin.

5. The pharmaceutical formulation of claim 1, wherein the analogue or derivative of angiotensin-(1-7) is a member selected from the group comprising Sar$^1$-Angiotensin-(1-7), D-Ala$^7$-Ang-(1-7) and D-Pro$^7$-Ang-(1-7).

6. A method for making a pharmaceutical formulation comprising Angiotensin-(1-7) peptide or an analogue or derivative thereof complexed with a hydrophilic cyclodextrin, comprising mixing a solution comprising a hydrophilic cyclodextrin with an aqueous solution of the peptide Angiotensin-(1-7) or an analogue or derivative thereof under conditions that permit the formation of the complex.

7. The method of claim 6, further comprising admixing an excipient selected from the group consisting of water, saline solution, buffer solution, dextrose solution, Hank's solution, and biocompatible saline solutions, with or without polyethylene glycol, oil, sesame oil, ethyloleate, trigiycerides, sodium carboxymethylcellulose, sorbitol, dextran, timerosal, m- or o-cresol, formalin, benzylalcohol, or serum albumin.

8. The method of claim 6, wherein said hydrophilic cyclodextrin is an alpha beta-, or gamma-cyclodextrin.

9. The method of claim 6, wherein the hydrophilic cyclodextrin is a member selected from the group comprising 6-O-maltosyl-, -cyclodextrin, sulfobutyl-, -cyclodextrin, 2-hydroxyethyl cyclodextrin, 2-hydroxypropyl cyclodextrin, 3-hydroxypropyl cyclodextrin, and 2,3-dihydroxypropyl cyclodextrin.

---

---

The invention claimed is:

1. A pharmaceutical formulation comprising Angiotensin-(1-7) or an analogue or derivative thereof complexed with a hydrophilic cyclodextrin.

2. The formulation of claim 1, wherein said formulation further comprises an excipient selected from the group consisting of water, saline solution, buffer solution, dextrose solution, Hank's solution, and biocompatible saline solutions, with or without polyethylene glycol, oil, sesame oil, ethyloleate, triglycerides, sodium carboxymethylcellulose, sorbitol, dextran, timerosal, m- or o-cresol, formalin, benzylalcohol, or serum albumin.

10. The method of claim 6, wherein the analogue or derivative of Angiotensin-(1-7) is a member selected from the group comprising Sar$^1$-Angiotensin-(1-7), D-Ala$^7$-Ang-(1-7) and D-Pro$^7$-Ang-( 1-7).

11. A method for treating arterial hypertension and its complications selected from the group consisting of endothelial dysfunction, left ventricular hypertrophy, myocardial ischemia, stroke, hypertensive retinopathy, cardiovascular arteriosclerosis and heart failure in an animal, comprising administering a therapeutically effective amount of a pharmaceutical formulation comprising Angiotensin-(1-7) or an analogue or derivative thereof complexed with a hydrophilic cyclodextrin.

12. The method of claim 11, wherein the analogue or derivative of angiotensin-(1-7) is a member selected from the group comprising Sar$^1$-Angiotensin-(1-7), D-Ala$^7$-Ang-(1-7) and D-Pro$^7$-Ang-(1-7).

13. The method of claim 11, wherein said hydrophilic cyclodextrin is an alpha beta-, or gamma-cyclodextrin.

14. The method of claim 11, wherein the hydrophilic cyclodextrin is a member selected from the group comprising 6-O-maltosyl-, -cyclodextrin, sulfobutyl-, -cyclodextrin, 2-hydroxyethyl cyclodextrin, 2-hydroxypropyl cyclodextrin, 3-hydroxypropyl cyclodextrin, and 2,3-dihydroxypropyl cyclodextrin.

15. The method of claim 11, wherein the animal is a human.

16. A method for treating a disease in an animal which is caused by a reduced production of Angiotensin-(1-7), comprising administering a therapeutically effective amount of a pharmaceutical formulation comprising Angiotensin-(1-7) or an analogue or derivative thereof complexed with a hydrophilic cyclodextrin.

17. The method of claim 16, wherein said hydrophilic cyclodextrin is an alpha beta-, or gamma-cyclodextrin.

18. The method of claim 16, wherein the hydrophilic cyclodextrin is a member selected from the group comprising 6-O-maltosyl-, -cyclodextrin, sulfobutyl-, -cyclodextrin, 2-hydroxyethyl cyclodextrin, 2-hydroxypropyl cyclodextrin, 3-hydroxypropyl cyclodextrin, and 2,3-dihydroxypropyl cyclodextrin.

19. The method of claim 16, wherein the analogue or derivative of Angiotensin-(1-7) is a member selected from the group comprising Sar$^1$-Angiotensin-(1-7), D-Ala$^7$-Ang-(1-7) and D-Pro$^7$-Ang-(1-7).

20. The method of claim 16, wherein the animal is a human.

21. A method for treating a disease in an animal caused by a reduced function or a reduced stimulation of the G-protein-coupled receptor MAS, comprising administering a therapeutically effective amount of a pharmaceutical formulation comprising Angiotensin-(1-7) or an analogue or derivative thereof complexed with a hydrophilic cyclodextrin.

22. The method of claim 21, wherein said hydrophilic cyclodextrin is an alpha beta-, or gamma-cyclodextrin.

23. The method of claim 21, wherein the hydrophilic cyclodextrin is a member selected from the group comprising 6-O-maltosyl-, -cyclodextrin, sulfobutyl-, -cyclodextrin, 2-hydroxyethyl cyclodextrin, 2-hydroxypropyl cyclodextrin, 3-hydroxypropyl cyclodextrin, and 2,3-dihydroxypropyl cyclodextrin.

24. The method of claim 21, wherein the analogue or derivative of Angiotensin-(1-7) is a member selected from the group comprising Sar$^1$-Angiotensin-(1-7), D-Ala$^7$-Ang-(1-7) and D-Pro$^7$-Ang-(1-7).

25. The method of claim 21, wherein the animal is a human.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Homo sapiens

<400> SEQUENCE: 1

Asp Arg Val Tyr Ile His Pro
1               5
```